United States Patent
Kosono et al.

(10) Patent No.: US 12,195,700 B2
(45) Date of Patent: Jan. 14, 2025

(54) LIQUID DETERGENT HAVING LOW VISCOSITY

(71) Applicant: AJINOMOTO CO., INC., Tokyo (JP)

(72) Inventors: Shuhei Kosono, Kawasaki (JP); Shun Kobayashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 587 days.

(21) Appl. No.: 17/380,080

(22) Filed: Jul. 20, 2021

(65) Prior Publication Data

US 2021/0348087 A1 Nov. 11, 2021

Related U.S. Application Data

(63) Continuation of application No. PCT/JP2020/003307, filed on Jan. 30, 2020.

(30) Foreign Application Priority Data

Jan. 31, 2019 (JP) ................................ 2019-016444

(51) Int. Cl.
| | |
|---|---|
| *A61K 8/00* | (2006.01) |
| *C11D 1/10* | (2006.01) |
| *C11D 1/66* | (2006.01) |
| *C11D 1/90* | (2006.01) |
| *C11D 3/04* | (2006.01) |
| *C11D 3/20* | (2006.01) |
| *C11D 17/00* | (2006.01) |

(52) U.S. Cl.
CPC ............ *C11D 17/0008* (2013.01); *C11D 1/10* (2013.01); *C11D 1/667* (2013.01); *C11D 1/90* (2013.01); *C11D 3/046* (2013.01); *C11D 3/2065* (2013.01); *C11D 17/0043* (2013.01); *C11D 2111/42* (2024.01)

(58) Field of Classification Search
None
See application file for complete search history.

(56) References Cited

U.S. PATENT DOCUMENTS

| | | | | |
|---|---|---|---|---|
| 6,444,629 B1 | * | 9/2002 | Elliott | ..................... C11D 3/373 |
| | | | | 510/156 |
| 2015/0141466 A1 | * | 5/2015 | Klug | ........................ A61K 8/44 |
| | | | | 510/130 |
| 2020/0078284 A1 | * | 3/2020 | Botto | ..................... A61K 8/375 |

FOREIGN PATENT DOCUMENTS

| | | | | |
|---|---|---|---|---|
| CA | 2078443 A1 | * | 9/1991 | |
| CN | 1064013 A | * | 9/1992 | ............... A61K 8/44 |
| JP | 2008-115137 A | | 5/2008 | |
| JP | 4527655 B2 | | 8/2010 | |
| JP | 2012-107147 A | | 6/2012 | |
| JP | 2013-108020 A | | 6/2013 | |
| JP | 2016-8206 A | | 1/2016 | |
| JP | 2016-17118 A | | 2/2016 | |
| JP | 2018-91 46 A | | 1/2018 | |
| JP | 2018-12650 A | | 1/2018 | |
| JP | 2019-112365 A | | 7/2019 | |
| WO | WO91/14759 | * | 10/1991 | |

OTHER PUBLICATIONS

International Search Report issued Apr. 7, 2020 in PCT/JP2020/003307 (with English translation), 6 pages.

* cited by examiner

*Primary Examiner* — Necholus Ogden, Jr.
(74) *Attorney, Agent, or Firm* — Oblon, McClelland, Maier & Neustadt, L.L.P.

(57) ABSTRACT

Liquid cleansing agents with a low viscosity, containing (A) one or more kinds selected from the group consisting of N-acyl acidic amino acid and a salt thereof, (B) one or more kinds selected from the group consisting of N-acyl neutral amino acid and a salt thereof, and (C) an amphoteric surfactant can be filled in a foamer container and are cleansing agents with high cleansing power which afford fine foam discharged from a foamer container, maintain fineness, provide a good amount of lather and a smooth feeling after washing, can prevent clogging in a foamer container during use at low temperatures, and are also superior in low temperature stability.

13 Claims, No Drawings

LIQUID DETERGENT HAVING LOW VISCOSITY

CROSS REFERENCES TO RELATED APPLICATIONS

This application is a continuation of International Patent Application No. PCT/JP2020/003307, filed on Jan. 30, 2020, and claims priority to Japanese Patent Application No. 2019-016444, filed on Jan. 31, 2019, both of which are incorporated herein by reference in their entireties.

BACKGROUND OF THE INVENTION

Field of the Invention

The present invention relates to liquid cleansing agents, more particularly, liquid cleansing agents optimal for use by filling in a foamer container.

Discussion of the Background

In recent years, as a cleansing agent for body or hair, a cleansing composition showing not only high detergency but also low irritancy to the skin and superior sense of use has been desired. Among others, amino acid type cleansing agent compositions are attracting attention. For example, cleansing agents using N-acylglutamate, N-acylglycine salt or the like as a cleansing composition have been considered (see JP-A-2018-9146, which is incorporated herein by reference in its entirety). Cleansing agents for body or hair are required to form fine foams and maintain fineness for a long time so that damages on the skin and hair during cleansing may be reduced. In general, however, anionic surfactants, including amino acid cleansing compositions, are more susceptible to ionization and repulsion of electric charges in the high pH range where cleansing power is considered to be high. As a result, problems occur in that the surfactant cannot be densely oriented at the gas-liquid interface, and production of fine bubbles becomes difficult.

A cleansing agent filled in a foamer container, which has become popular in recent years, can be discharged with ease as creamy foam by extrusion from the container after passage through a mesh inside the foamer container. Therefore, cleansing agents in foamers with superior usability are used as various cleansing agents such as facial cleanser, hair shampoo, and hand soap.

For example, a cleansing composition in a foamer container containing at least any surfactant selected from an N-acylamino acid anionic surfactant, other anionic surfactant with a Krafft point of not less than 20° C., an amphoteric surfactant, and a semipolar surfactant, polyhydric alcohol, and a non-ionic surfactant has been proposed, which composition is creamy, elastic, superior in stability at low temperatures, and gives a moist skin texture after washing (see JP-B-4527655, which is incorporated herein by reference in its entirety).

In addition, a liquid cleansing composition containing a higher fatty acid, an N-acylamino acid surfactant, alkyl polyglucoside, and a Rita extract has also been proposed, which composition is free of clogging, affords creamy and stable foam, is superior in foam formation even at low temperatures, and superior in a refreshing feeling after rinsing and a moist feeling after towel drying (see JP-A-2016-17118, which is incorporated herein by reference in its entirety).

Furthermore, a liquid cleansing composition in a foamer container, containing an N-acylglycine surfactant, an amphoteric surfactant and/or a semipolar surfactant, a higher fatty acid soap, and a polyhydric alcohol has been proposed, which composition achieves creamy and elastic foam quality, alleviates skin irritation, can give refreshing skin texture without a feeling of tension, has superior stability at low temperatures, and does not cause clogging and the like (see JP-A-2012-107147, which is incorporated herein by reference in its entirety).

However, there is a room for improvement in order to simultaneously achieve foam characteristics such as the fineness and retention of the foam discharged from a foamer container, the lather amount after rubbing and the like even in a high pH range, sense of use such as smooth feeling after washing and the like, maintaining the discharge property of foam from a foamer container during use at low temperatures, and low temperature stability. Furthermore, a problem is known that a cleansing agent used for a foamer container causes clogging in the mesh inside the container.

SUMMARY OF THE INVENTION

Accordingly, it is an object of the present invention to provide liquid cleansing compositions with low viscosity that can be filled in a foamer container.

It is another object of the present invention to provide cleansing agents with high cleansing power which afford fine foam discharged from a foamer container irrespective of the pH region, maintain fineness, provide a good amount of lather and a smooth feeling after washing, can prevent clogging in a foamer container during use at low temperatures, and are also superior in low temperature stability.

These and other objects, which will become apparent during the following detailed description, have been achieved by the present inventor's discovery that a cleansing agent with low stimulation which produces fine foam even in a high pH region and is superior in sense of use can be obtained by combining an N-acyl acidic amino acid surfactant, an N-acyl neutral amino acid surfactant, and an amphoteric surfactant, and also found that the cleansing agent has a low viscosity and suppresses clogging even when filled in a foamer container, and can further provide a liquid cleansing composition superior in low temperature stability, which resulted in the completion of the present invention.

Accordingly, the present invention provides the following.

(1-1) A liquid cleansing agent with a low viscosity, comprising (A) one or more kinds selected from the group consisting of N-acyl acidic amino acid and a salt thereof, (B) one or more kinds selected from the group consisting of N-acyl neutral amino acid and a salt thereof, and (C) an amphoteric surfactant.

(1-2) A liquid cleansing agent with a low viscosity, comprising (A) one or more kinds selected from the group consisting of N-acyl acidic amino acid and a salt thereof, (B) one or more kinds selected from the group consisting of N-acyl neutral amino acid and a salt thereof, and (C) an amphoteric surfactant, and having
a viscosity at 25° C. of less than 150 mPa·s
and a pH of 6.5 to 13.

(2-1) The liquid cleansing agent of (1), wherein the pH is 7 to 13.

(2-2) The liquid cleansing agent of (1), wherein the pH is 8 to 11.

(3) The liquid cleansing agent of (1) or (2), wherein the acidic amino acid of component (A) is glutamic acid.

(4) The liquid cleansing agent of any of (1) to (3), wherein the neutral amino acid of component (B) is glycine.
(5) The liquid cleansing agent of any of (1) to (4), wherein the acyl group of component (A) and the acyl group of component (B) are cocoyl groups.
(6) The liquid cleansing agent of any of (1) to (5), wherein the aforementioned component (C) is one or more kinds selected from the group consisting of alkylamide hydroxysulfobetaine, alkylhydroxysulfobetaine, imidazolinium betaine, alkylbetaine and a fatty acid amide propylbetaine surfactant.
(7) The liquid cleansing agent of any of (1) to (5), wherein the aforementioned component (C) is one or more kinds selected from the group consisting of cocamide propylbetaine, lauramide propylbetaine, disodium cocoamphodiacetate, sodium cocoamphoacetate, sodium lauroamphoacetate, cocobetaine, lauryl hydroxysulfobetaine, and lauramide propylhydroxysulfobetaine.
(8) The liquid cleansing agent of any of (1) to (7), wherein a weight proportion of a total content of the aforementioned components (A) and (B) to a content of component (C) ((A)+(B))/(C) is 0.4 to 10.
(9) The liquid cleansing agent of any of (1) to (8), wherein the content of the aforementioned component (A) is not less than 2 wt % and not more than 10 wt %.
(10) The liquid cleansing agent of any of (1) to (9), wherein the content of the aforementioned component (B) is not less than 1 wt % and not more than 10 wt %.
(11) The liquid cleansing agent of any of (1) to (10), wherein the content of the aforementioned component (C) is not less than 1 wt % and not more than 20 wt %.
(12) The liquid cleansing agent of any of (1) to (11), further comprising component (D) fatty acid or a salt thereof.
(13) The liquid cleansing agent of any of (1) to (12), further comprising component (E) polyhydric alcohol.
(14) The liquid cleansing agent of any of (1) to (13), further comprising component (F) non-ionic surfactant.
(15) The liquid cleansing agent of any of (1) to (14), further comprising component (G) sodium chloride.
(16) The liquid cleansing agent of any of (12) to (15), wherein a weight proportion of a content of component (D) to a content of component (B) (D)/(B) is more than 0 and not more than 3.
(17) The liquid cleansing agent of any of (1) to (16), for use in a foamer container.
(18) The liquid cleansing agent of any of (1) to (17), for skin or hair.

Advantageous Effects of Invention

According to the present invention, a liquid cleansing agent can be provided which has a high cleansing power and generates fine foam capable of maintaining fineness in a good lather amount when discharged from a foamer container.

According to the present invention, a liquid cleansing agent with low stimulation and superior in sense of use by affording a smooth feeling after washing can be provided.

According to the present invention, a liquid cleansing agent can be provided which is superior in low temperature stability and can prevent clogging during use at low temperatures even when filled in a foamer container.

DETAILED DESCRIPTION OF THE PREFERRED EMBODIMENTS

The present invention relates to a liquid cleansing agent with a low viscosity, comprising (A) one or more kinds selected from the group consisting of N-acyl acidic amino acid and a salt thereof, (B) one or more kinds selected from the group consisting of N-acyl neutral amino acid and a salt thereof, and (C) an amphoteric surfactant (hereinafter sometimes to be abbreviated as the liquid cleansing agent of the present invention).

In the present invention, the low viscosity means a viscosity of less than 150 mPa·s at 25° C., from the aspect of a foamer container during use, it is preferably less than 120 mPa·s, more preferably less than 100 mPa·s. The lower limit of the viscosity is not particularly limited and not less than 1 mPa·s can be mentioned. The viscosity can be measured by a conventional method, and the viscosity of a liquid cleansing agent at 25° C. can be measured using, for example, a TYPE B viscometer.

Examples of the method for setting the viscosity in the present invention to fall within the above-mentioned range include a method for setting pH of a cleansing composition at 25° C. to not less than 6.5 and a concentration of a surfactant in the cleansing composition to not more than 20%.

As component (A) N-acyl acidic amino acid and a salt thereof in the present invention, any of D form, L form and DL form can be used. Each of the N-acyl acidic amino acid and a salt thereof may be used alone, or a mixture of two or more kinds thereof at any ratio may be used.

The acyl group of component (A) N-acyl acidic amino acid or a salt thereof in the present invention is an acyl group induced from fatty acid having 8 to 22 carbon atoms, and an acyl group induced from fatty acid having 8 to 20 carbon atoms is preferable, and an acyl group induced from fatty acid having 8 to 18 carbon atoms is more preferable. For example, an acyl group derived from lauric acid, myristic acid, palmitic acid, stearic acid, oleic acid, isostearic acid or the like, a mixture thereof such as beef tallow fatty acid, coconut oil fatty acid, palm kernel oil fatty acid and the like can be mentioned. A lauroyl group, a myristoyl group, an acyl group induced from coconut oil fatty acid (cocoyl group) is preferred, and a cocoyl group is more preferred.

While the acidic amino acid of component (A) in the present invention is not particularly limited as long as it is an acidic amino acid, examples thereof include glutamic acid, aspartic acid and the like, and glutamic acid is preferred.

As a salt of N-acyl acidic amino acid, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salts of basic organic substances and the like can be mentioned. Of these, alkali metal salt and alkanolamine salt are preferred, and sodium salt, potassium salt, and triethanolamine salt are more preferred, since one superior in foamability and preservation stability is obtained.

As a salt of N-acyl acidic amino acid, a mono salt or a disalt is preferred.

Component (A) may be in the form of a salt, which is obtained by adding, when the liquid cleansing agent of the present invention is prepared, N-acyl acidic amino acid together with a substance (e.g., sodium hydroxide, potassium hydroxide, TEA etc.) that forms the above-mentioned salts, thus performing neutralization. Furthermore, component (A) may contain unneutralized N-acyl acidic amino acid.

Specific examples of the N-acyl acidic amino acid salt to be used in the present invention include monosodium salt, disodium salt, monopotassium salt, dipotassium salt, triethanolamine salt and the like of N-lauroylglutamic acid, N-myristoylglutamic acid, N-cocoyl (coconut oil fatty acid acyl) glutamic acid, N-lauroylaspartic acid, N-myristoylaspartic acid or N-cocoylaspartic acid. One kind of these may be used or a mixture of two or more kinds thereof may be used. Among these, monosodium salt, disodium salt, monopotassium salt, dipotassium salt, or triethanolamine salt of N-cocoyl glutamic acid, or a mixture thereof is preferred.

Component (B) N-acyl neutral amino acid and a salt thereof of the present invention may each be used alone, or a mixture of two or more kinds thereof at an optional ratio may be used.

The acyl group of component (B) N-acyl neutral amino acid in the present invention is an acyl group induced from a fatty acid having 8 to 22 carbon atoms, an acyl group induced from a fatty acid having 8 to 20 carbon atoms is preferable, and an acyl group induced from a fatty acid having 8 to 18 carbon atoms is more preferable.

For example, an acyl group induced from lauric acid, myristic acid, palmitic acid, stearic acid, oleic acid, isostearic acid and the like, or a mixture thereof such as beef tallow fatty acid, coconut oil fatty acid, palm kernel oil fatty acid and the like can be mentioned. A lauroyl group, a myristoyl group or an acyl group induced from a lauroyl group, a myristoyl group, or coconut oil fatty acid (cocoyl group or coconut oil fatty acid acyl group) is preferred from the aspects of foam retention and usability at low temperatures, and a cocoyl group is more preferred.

The neutral amino acid of component (B) in the present invention is not particularly limited as long as it is a neutral amino acid, and glycine, alanine, threonine, valine, leucine, isoleucine, phenylalanine, serine, proline and the like can be used. In the case of an amino acid having an optically active center other than glycine, any of L form, D form, and DL form may be used. Among these, one kind may be used, or two or more kinds selected from the above-mentioned group may be used as a mixture. In view of good foaming and mildness to the skin, glycine and alanine are preferred, and glycine is more preferred.

As a salt of N-acyl neutral amino acid, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine salt and the like; ammonium salt; and salts of basic organic substances and the like can be mentioned.

Among these, alkali metal salt is preferred, a sodium salt and potassium salt are more preferred, and a potassium salt is more preferred, from the aspect of long-term preservation stability.

Component (B) may be in the form of a salt by neutralizing by adding together with N-acyl neutral amino acid and a substance (e.g., sodium hydroxide, potassium hydroxide, TEA etc.) that forms the above-mentioned salt when the liquid cleansing agent of the present invention is prepared.

Furthermore, component (B) may contain unneutralized N-acyl neutral amino acid.

Specifically, N-cocoyl (coconut oil fatty acid acyl) glycine potassium, N-cocoylglycine sodium and the like can be mentioned, and N-cocoylglycine potassium is preferred among these.

As component (C) amphoteric surfactant in the present invention,
(1) aminoacetic acid betaine surfactants (e.g., alkylamide hydroxysulfobetaine such as lauroylamide propylhydroxysulfobetaine and the like, alkylhydroxysulfobetaine such as lauryl hydroxysulfobetaine and the like, lauryl dimethyl amino acetic acid betaine, coconut oil dimethyl amino acetic acid betaine, coconut oil fatty acid dimethyl amino acetic acid betaine, lauroylamide propyldimethyl amino acetic acid betaine, hydroxyalkyl(C12-14)hydroxyethylsarcosine etc.),
(2) imidazolinium betaine surfactants (e.g., sodium salt of cocoamphoacetic acid, lauroamphoacetic acid, cocoamphodiacetic acid, lauroamphodiacetic acid, lauraminopropionic acid and the like),
(3) alkylbetaine surfactants (cocobetaine, lauryl betaine etc.),
(4) fatty acid amide propylbetaine surfactants (e.g., cocamidepropyl betaine, lauramidepropyl betaine, myristamidopropyl betaine etc.),
and the like can be mentioned.

Among these, cocamide propylbetaine, lauramide propylbetaine, disodium cocoamphodiacetate, sodium cocoamphoacetate, sodium lauroamphoacetate, cocobetaine, lauryl hydroxysulfobetaine (lauryl hydroxysultaine), and lauramide propylhydroxysulfobetaine (lauramide propylhydroxysultaine) are preferred from the aspects of the fineness of the foam discharged from a foamer container, and fineness of foam during rubbing.

In the present invention, the total content of (A), (B) and (C) is within the range of generally 4 to 30 wt %, preferably 4 to 20 wt %, more preferably 5 to 15 wt %, with respect to the total amount of the cleansing agent, from the aspect of the prevention of clogging in the foamer container.

In the cleansing agent of the present invention, the weight proportion (to be also referred to as weight ratio) of the content of (A) per 1 part by weight of (B) is generally 0.5 to 4 parts by weight, preferably 1 to 3 parts by weight, from the aspects of a smooth feeling after washing and stability at low temperatures.

In the cleansing agent of the present invention, the weight proportion of the total content of components (A) and (B) to the content of component (C) ((A)+(B))/(C) is generally 0.4 to 10, preferably 0.9 to 8, more preferably 0.9 to 5.5, further preferably 1 to 4, from the aspects of foam retention and lather amount after rubbing.

In the cleansing agent of the present invention, the content of component (A) is generally not less than 2 wt % and not more than 10 wt %, preferably 2 to 9 wt %, more preferably 3 to 8.4 wt %, from the aspects of foam retention and a smooth feeling after washing.

In the cleansing agent of the present invention, the content of component (B) is generally not less than 1 wt % and not more than 10 wt %, preferably 1 to 5 wt %, more preferably 1 to 4 wt %, from the aspects of foam retention, a smooth feeling after washing, and lather amount after rubbing.

In the cleansing agent of the present invention, the content of component (C) is generally not less than 1 wt % and not more than 20 wt %, preferably 2 to 15 wt %, more preferably 2 to 12 wt %, from the aspects of foam retention and lather amount after rubbing.

The cleansing agent of the present invention may contain component (D) a fatty acid or a salt thereof from the aspect of lather amount after rubbing.

As the fatty acid, saturated or unsaturated fatty acid having 8 to 22 carbon atoms, and caprylic acid, capric acid, lauric acid, myristic acid, stearic acid, isostearic acid, palmitic acid, oleic acid, linoleic acid, behenic acid, coconut oil fatty acid, coconut oil fatty acid, palm kernel fatty acid, hardened beef tallow fatty acid and the like can be specifically mentioned. One kind of these may be used or a mixture of two or more kinds selected from the above-mentioned group may be used. Particularly, coconut oil fatty acid is preferred.

Specific examples of the fatty acid salt include sodium salt, potassium salt, arginine salt, and the like of the above-mentioned fatty acid, and coconut oil fatty acid potassium and the like are preferred.

One kind or two or more kinds of component (D) fatty acid or a salt thereof can be used in combination. In addition, (D) fatty acid or a salt thereof is desirably blended in a cleansing agent in a proportion of generally 0 to 8 wt %, preferably 0 to 5 wt %, of the cleansing agent.

In the cleansing agent of the present invention, the weight proportion of the content of component (D) to the content of component (B) (D)/(B) is generally more than 0 and not more than 3, preferably more than 0 and not more than 1.5, more preferably more than 0 and not more than 0.6, further preferably more than 0 and not more than 0.5, from the aspects of a smooth feeling after washing and foam retention.

The cleansing agent of the present invention may contain component (E) a polyhydric alcohol from the aspects of a smooth feeling after washing and foam retention.

As polyhydric alcohol, glycerols such as glycerin, diglycerin, polyglycerin and the like, sugar alcohols such as sorbitol, erythritol, xylitol and the like, glycols such as isopreneglycol, 1,2-propylene glycol (PG), dipropylene glycol (DPG), ethoxydiglycol, 1,3-butyleneglycol (BG) and the like can be mentioned. These may be used alone or a mixture of two or more kinds thereof may be used. Among these, glycerols and glycols are preferred, and glycerin, DPG, BG, PG and the like are more preferred.

One kind or two or more kinds of component (E) polyhydric alcohol can be used in combination. (E) polyhydric alcohol is desirably blended in a cleansing agent in a proportion of generally 0 to 30 wt %, preferably 0 to 25 wt %, of the cleansing agent.

The cleansing agent of the present invention may contain component (F) a non-ionic surfactant from the aspect of stability at low temperatures.

As the non-ionic surfactant, esters such as glyceryl fatty acid ester, sorbitan fatty acid ester, sucrose fatty acid ester and the like, ethers such as alkylpolyethylene glycol, polyoxyethylene alkylphenylether and the like, alkylglycoside and the like can be mentioned. Among these, an ester surfactant or ether surfactant is preferred, sorbitan fatty acid ester or alkylpolyethylene glycol is more preferred, and mono lauric acid sorbitan polyoxyethylene or polyoxyethylene (30)polyoxypropylene (6) decyltetradecylether (PPG-6 decyltetradeceth-30) is more preferred.

One kind or two or more kinds of component (F) non-ionic surfactant can be used in combination. (F) non-ionic surfactant is desirably blended in a cleansing agent in a proportion of generally 0 to 10 wt %, preferably 0 to 8 wt %, of the cleansing agent.

The cleansing agent of the present invention may contain (G) sodium chloride from the aspect of the creaminess of the foam discharged from a foamer container. (G) sodium chloride is desirably blended in a cleansing agent in a proportion of generally 0 to 5 wt %, preferably 0 to 2 wt %, of the cleansing agent.

As (A) to (G) in the present invention, synthesized products and commercially available products can be used.

The liquid cleansing agent of the present invention is a liquid using water, surfactant, polyhydric alcohol or the like as a medium. A cleansing agent obtained by blending a solid content containing the above-mentioned components with water and the like to give a liquid cleansing agent is also included in the liquid cleansing agent of the present application. That is, a cleansing agent to be prepared at the time of use, before use as a liquid cleansing agent, is also a concept included in the liquid cleansing agent of the present invention.

The liquid cleansing agent of the present invention can be produced by a method known per se. For example, a mixture of the above-mentioned respective components and other additives are mixed, and the mixture is generally heated at 20 to 60° C. for 1 min to 10 min to uniformly dissolve each component, whereby the liquid cleansing agent can be obtained.

Various generally-used additives can be added to the liquid cleansing agent of the present invention as long as the effect of the invention is not inhibited.

For example, starting materials and the like described in various official compendia such as Japanese Standards of Cosmetic Ingredients, Cosmetic Ingredients Codex, Japanese Standard of Quasi-drug Ingredients, the Japanese Pharmacopoeia, Japanese Standards for Pharmaceutical Ingredient, Japan's Specifications and Standards for Food Additives (all of which are incorporated herein by reference in their entireties) and the like, such as higher alcohol such as cetyl alcohol, stearyl alcohol, behenyl alcohol, isostearyl alcohol, octyldodecanol, oleyl alcohol, myristyl alcohol and the like, humectant such as trimethylglycine and the like, surfactant such as anionic surfactant other than component (A), cationic surfactant and the like, synthetic fats and oils such as vegetable oil, animal fat, natural fat derivative, mineral fat, lower and higher fatty acid ester, N-acylglutamic acid ester and the like; silicone compound; polymer substance; animal or plant extract; amino acid; nucleic acid; vitamin; enzyme; anti-inflammatory agent; antimicrobial agent; preservative; antioxidant; ultraviolet absorber; chelating agent; adiaphoretic; oxidation dye; pH adjuster; pearly sheen agent; and the like can be mentioned.

The pH of the liquid cleansing agent of the present invention is generally from weak acidic to basic, and desirably adjusted to preferably 6.5 to 13, preferably 7 to 13, more preferably 7 to 11, further preferably 8 to 11, from the aspects of stability at low temperatures and prevention of clogging of mesh at low temperatures.

As used herein, the pH of the liquid cleansing agent of the present invention is defined to be the pH of a 10 to 15 wt % aqueous solution (25° C.)

The liquid cleansing agent of the present invention can be used by filling in a container used generally. It is preferable to use the agent filled in a foamer container because good foamability and good foam stability can be achieved.

The foamer container to be filled with the liquid cleansing agent of the present invention is not particularly limited and, for example, discharge containers such as non-aerosol containers (e.g., squeeze foamer, pump foamer, etc.) and aerosol containers (e.g., aerosol can, etc.), and the like can be mentioned. A non-aerosol container is preferred because it has a simple mechanism and is environmentally friendly without requiring a propellant.

The liquid cleansing agent of the present invention can be used for cleansing agents for skin or hair, such as shampoo, facial cleanser, body shampoo, hand soap, shaving agent, and the like, cleansing agents for kitchen and laundry detergents.

Other features of the invention will become apparent in the course of the following descriptions of exemplary embodiments which are given for illustration of the invention and are not intended to be limiting thereof.

EXAMPLES

Unless otherwise specified, the blending amounts in the following Examples and Comparative Examples indicate the solid content (wt %) of the surfactant.

The liquid cleansing compositions shown in Tables 1 to 5 were prepared in a laboratory controlled to 25° C., and filled in 600-mL foamer containers (Daiwa Can Company, net 200 mesh, 100 mesh, 1 sheet each) to obtain liquid cleansing compositions in former containers. The obtained liquid cleansing compositions were subjected to the evaluations in (1) and (2), and the results thereof are shown in Tables 1 to 6.

(1) Fineness of Foam

For the measurement of the fineness of sample foam, a dynamic foam analyzer (Dynamic Foam Analyzer (DFA100), manufactured by KRUSS) was used as a measuring device. First, 6.0 g of each sample was discharged from the foamer container into a measuring cylinder with a prism for the measurement. Then, the sample was poured into the measuring cylinder and the measuring cylinder was installed on the measurement pedestal. Using an accessory device (Foam Structure Module (PA4570), manufactured by KRUSS) that can measure the number of foams per unit area over time, the number of foams per 1 $mm^2$ was measured at a height of 195 cm and evaluated according to the following criteria.

Judgment Criteria

A: number of foams per 1 $mm^2$ after 40 seconds is not less than 55
B: number of foams per 1 $mm^2$ after 40 seconds is not less than 45 and less than 55
C: number of foams per 1 $mm^2$ after 40 seconds is less than 45

(2) Foam Retention

For the measurement of the foam retention of the samples, a dynamic foam analyzer (Dynamic Foam Analyzer (DFA100), manufactured by KRUSS) was used as a measuring device. First, 6.0 g of each sample was discharged from the foamer container into a measuring cylinder with a prism for the measurement. Then, the sample was poured into the measuring cylinder and the measuring cylinder was installed on the measurement pedestal. Using an accessory device (Foam Structure Module (PA4570), manufactured by KRUSS) that can measure the number of foams per unit area over time, the number of foams per 1 $mm^2$ was measured at a height of 195 cm and evaluated according to the following criteria.

Judgment Criteria

A: rate of decrease in fineness of foam from 40 seconds later to 480 seconds later is less than 54.9%
B: rate of decrease in fineness of foam from 40 seconds later to 480 seconds later is not less than 54.9% and less than 65%
C: rate of decrease in fineness of foam from 40 seconds later to 480 seconds later is not less than 65%

The liquid cleansing compositions shown in Tables 1-5 were prepared in a laboratory controlled to 25° C., and filled in 100-mL foamer containers (Takemoto Yohki Co., Ltd., net 200 mesh, 100 mesh, 1 sheet each) to obtain liquid cleansing compositions in former containers. The obtained liquid cleansing compositions were subjected to the evaluations in (3) to (6), and the results thereof are shown in Tables 1 to 6.

(3) Smooth Feeling after Washing

Two pushes (about 0.7 mL) of the sample filled in each container were taken on the palm, and the palms of both hands were rubbed together for 15 sec, and sensory evaluation of the smooth feeling of the skin after washing was performed by one expert panel based on the following evaluation criteria.

Judgment Criteria

A: very smooth feeling
B: slightly smooth feeling
C: no smooth feeling (4) Lather Amount after Rubbing Two pushes (about 0.7 mL) of the sample filled in each container were taken on the palm, and the palms of both hands were rubbed together for 15 sec, and the lather amount after rubbing was evaluated based on the following evaluation criteria.

A: very large amount of foam
B: slightly large amount of foam
C: small lather amount (5) Low Temperature Stability Each of the prepared samples was filled in a 10 mL transparent glass vial, stored at −5° C., and crystal precipitation and the state of separation and discoloration after 10 days were visually evaluated based on the following criteria.

Judgment Criteria

A: crystal precipitation, separation or discoloration is not observed at all at −5° C.
B: crystal precipitation, separation or discoloration is slightly observed at −5° C., but precipitation, separation or discoloration of crystal is not observed at all when returned to room temperature
C: crystal precipitation, separation or discoloration is clearly observed even after allowing to return to room temperature (6) Clogging of Mesh after Storage at Low Temperature Twenty pushes of the sample filled in each container were discharged, and stored in a thermostatic tank at −5° C. for 10 days. After 1, 4 and 10 days from the day of start of the storage, 20 pushes of samples were discharged from each container horizontally from a height of 40 cm, and the clogging of the mesh under low temperature conditions was evaluated based on the following criteria. By causing clogging, the discharge of foam from the foamer container becomes hard, and the flying distance of the foam becomes short.

Judgment Criteria

A: average flying distance is not less than 40 cm when sample is discharged by 20 pushes immediately after taking out the sample from a thermostatic tank at −5° C.
B: average flying distance is less than 40 cm when sample is discharged by 20 pushes immediately after taking out from a thermostatic tank at −5° C. but not less than 40 cm when the sample is discharged by 20 pushes after allowing to return to room temperature
C: average flying distance is less than 40 cm both when sample is discharged by 20 pushes immediately after taking out from a thermostatic tank at −5° C. and after allowing to return to room temperature (7) Comprehensive Evaluation A comprehensive evaluation was made based on the following evaluation criteria wherein A is 5 points, B is 4 points, and C is 1 point.

Judgment Criteria

A: not less than 28 points
B: not less than 25 points and not more than 27 points
C: not more than 24 points

TABLE 1

|  |  | Ex. 1 | Ex. 2 | Ex. 3 | Ex. 4 | Ex. 5 | Ex. 6 | Ex. 7 | Ex. 8 |
|---|---|---|---|---|---|---|---|---|---|
| component (A) | sodium cocoyl glutamate *1 | 6.6 | 6.6 | 6.6 | 6.6 | 6.6 | 6.6 | 6.6 | 6.6 |
| component (B) | potassium cocoyl glycinate *2 | 3.3 | 3.3 | 3.3 | 3.3 | 3.3 | 3.3 | 3.3 | 3.3 |
| component (C) | cocamide propylbetaine *3 | 5.0 | | | | | | | |
| | lauramide propylbetaine *4 | | 5.0 | | | | | | |
| | disodium cocoamphodiacetate *5 | | | 5.0 | | | | | |
| | sodium cocoamphoacetate *6 | | | | 5.0 | | | | |
| | sodium lauroamphoacetate *7 | | | | | 5.0 | | | |
| | cocobetaine *8 | | | | | | 5.0 | | |
| | lauryl hydroxysultaine *9 | | | | | | | 5.0 | |
| | lauramide propylhydroxysultaine *10 | | | | | | | | 5.0 |
| common portion | KOH | as appropriate | as appropriate | as appropriate | as appropriate | as appropriate | as appropriate | as appropriate | as appropriate |
| | water | rest | rest | rest | rest | rest | rest | rest | rest |
| | pH | 9.0 | 9.0 | 9.0 | 9.0 | 9.0 | 9.0 | 9.0 | 9.0 |
| | total (wt %) | 100.0 | 100.0 | 100.0 | 100.0 | 100.0 | 100.0 | 100.0 | 100.0 |
| | surfactant solid content percentage (%) | 15.0 | 15.0 | 15.0 | 15.0 | 15.0 | 15.0 | 15.0 | 15.0 |
| | weight ratio (A + B)/C | 2.0 | 2.0 | 2.0 | 2.0 | 2.0 | 2.0 | 2.0 | 2.0 |
| sense of use evaluation results | (1) fineness of foam | A | A | A | A | A | A | A | A |
| | (2) foam retention | A | A | A | A | A | A | A | A |
| | (3) smooth feeling after washing | A | A | A | A | A | A | A | A |
| | (4) lather amount after rubbing | A | A | A | A | A | A | A | A |
| | (5) low temperature stability | A | A | A | A | A | A | A | A |
| | (6) clogging of mesh under low temperature conditions | A | A | A | A | A | A | A | A |
| | Comprehensive evaluation | A | A | A | A | A | A | A | A |

TABLE 2

|  |  | Ex. 9 | Ex. 10 | Ex. 11 | Ex. 12 | Ex. 13 | Ex. 14 | Ex. 15 | Ex. 16 | Ex. 17 | Ex. 18 | Ex. 19 |
|---|---|---|---|---|---|---|---|---|---|---|---|---|
| component (A) | sodium cocoyl glutamate *1 | 8.4 | 8.2 | 8.0 | 7.3 | 6.0 | 5.1 | 3.3 | 6.0 | 6.0 | 6.0 | 6.0 |
| component (B) | potassium cocoyl glycinate *2 | 4.2 | 4.1 | 4.0 | 3.6 | 3.0 | 2.5 | 1.6 | 3.0 | 3.0 | 3.0 | 3.0 |
| component (C) | cocamide propylbetaine *3 | 2.3 | 2.7 | 3.0 | 4.0 | 6.0 | 7.4 | 10.0 | 6.0 | 6.0 | 6.0 | 6.0 |
| | sodium cocoamphoacetate *6 | | | | | | | | | | | |
| | sodium lauroamphoacetate *7 | | | | | | | | | | | |
| component (E) | glycerin | | | | | | | | | 3.0 | 10.0 | |
| component (F) | polysorbate 20 | | | | | | | | | | | 1.0 |
| component (G) | NaCl | | | | | | | | 1.5 | | | |
| common portion | citric acid | | | | | | | | | | | |
| | KOH | as appropriate | as appropriate | as appropriate | as appropriate | as appropriate | as appropriate | as appropriate | as appropriate | as appropriate | as appropriate | as appropriate |
| | water | rest | rest | rest | rest | rest | rest | rest | rest | rest | rest | rest |
| | pH | 9.0 | 9.0 | 9.0 | 9.0 | 9.0 | 9.0 | 9.0 | 9.0 | 9.0 | 9.0 | 9.0 |
| | total (wt %) | 100.0 | 100.0 | 100.0 | 100.0 | 100.0 | 100.0 | 100.0 | 100.0 | 100.0 | 100.0 | 100.0 |
| | surfactant solid content percentage (%) | 14.9 | 15.0 | 15.0 | 14.9 | 15.0 | 15.0 | 14.9 | 15.0 | 15.0 | 15.0 | 15.0 |
| | weight ratio (A + B)/C | 5.5 | 4.6 | 4.0 | 2.7 | 1.5 | 1.0 | 0.5 | 1.5 | 1.5 | 1.5 | 1.5 |
| sense of use evaluation results | (1) fineness of foam | A | A | A | A | A | A | A | A | A | A | A |
| | (2) foam retention | A | B | A | A | A | A | A | B | A | A | B |
| | (3) smooth feeling after washing | A | A | A | A | A | A | B | A | A | A | A |
| | (4) lather amount after rubbing | B | A | A | A | A | A | B | A | A | A | A |
| | (5) low temperature stability | A | A | A | A | A | A | A | A | A | A | A |
| | (6) clogging of mesh under low temperature conditions | A | A | A | A | A | A | A | A | A | A | A |
| | Comprehensive evaluation | A | A | A | A | A | A | A | A | A | A | A |

TABLE 3

|  |  | Ex. 20 | Ex. 21 | Ex. 22 | Ex. 23 | Ex. 24 | Ex. 25 | Ex. 26 | Ex. 27 | Ex. 28 | Ex. 29 |
|---|---|---|---|---|---|---|---|---|---|---|---|
| component (A) | sodium cocoyl glutamate *1 | 4.8 | 3.0 | 4.8 | 3.0 | 6.6 | 6.6 | 6.6 | 6.6 | 6.6 | 6.6 |
| component (B) | potassium cocoyl glycinate *2 | 2.4 | 1.5 | 2.4 | 1.5 | 3.3 | 3.3 | 3.3 | 3.3 | 3.3 | 3.3 |
| component (C) | cocamide propylbetaine *3 | 7.8 | 10.5 |  |  | 5.0 | 5.0 | 5.0 | 5.0 | 5.0 | 5.0 |
|  | sodium cocoamphoacetate *6 |  |  |  | 7.8 |  |  |  |  |  |  |
|  | sodium lauroamphoacetate *7 |  |  | 7.8 |  |  |  |  |  |  |  |
| component (E) | glycerin |  |  |  |  |  |  |  |  |  |  |
| component (F) | polysorbate 20 |  |  |  |  |  |  |  |  |  |  |
| component (G) | NaCl |  |  |  |  |  |  |  |  |  |  |
| common portion | citric acid |  | as appropriate | as appropriate | as appropriate |  |  |  |  |  |  |
|  | KOH | as appropriate |  |  |  | as appropriate | as appropriate | as appropriate | as appropriate | as appropriate | as appropriate |
|  | water | rest | rest | rest | rest | rest | rest | rest | rest | rest | rest |
|  | PH | 7.0 | 7.0 | 7.5 | 7.5 | 8.0 | 8.5 | 9.0 | 9.5 | 10.0 | 11.0 |
|  | total (wt %) | 100.0 | 100.0 | 100.0 | 100.0 | 100.0 | 100.0 | 100.0 | 100.0 | 100.0 | 100.0 |
|  | surfactant solid content percentage (%) | 15.0 | 15.0 | 15.0 | 15.0 | 15.0 | 15.0 | 15.0 | 15.0 | 15.0 | 15.0 |
|  | weight ratio (A + B)/C | 0.9 | 0.4 | 0.9 | 0.6 | 2.0 | 2.0 | 2.0 | 2.0 | 2.0 | 2.0 |
| sense of use evaluation results | (1) fineness of foam | A | A | A | A | A | A | A | A | A | A |
|  | (2) foam retention | B | B | B | B | B | B | A | A | A | B |
|  | (3) smooth feeling after washing | A | A | A | A | A | A | A | A | A | A |
|  | (4) lather amount after rubbing | A | A | B | A | A | A | A | A | A | A |
|  | (5) low temperature stability | A | A | A | A | A | A | A | A | A | A |
|  | (6) clogging of mesh under low temperature conditions | A | A | A | A | A | A | A | A | A | B |
| Comprehensive evaluation |  | A | A | A | A | A | A | A | A | A | A |

TABLE 4

|  |  | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|
| component (A) | sodium cocoyl glutamate *1 | 10.0 | 8.0 | 7.3 | 6.6 | 6.0 | 5.3 | 4.0 |
| component (B) | potassium cocoyl glycinate *2 |  | 2.0 | 2.7 | 3.3 | 4.0 | 4.7 | 6.0 |
| component (C) | lauramide propylbetaine *4 |  |  |  |  |  |  |  |
|  | disodium cocoamphodiacetate *5 |  |  |  |  |  |  |  |
|  | sodium cocoamphoacetate *6 |  |  |  |  |  |  |  |
|  | sodium lauroamphoacetate *7 |  |  |  |  |  |  |  |
|  | cocobetaine *8 |  |  |  |  |  |  |  |
|  | lauramide propylhydroxy-sultaine *10 |  |  |  |  |  |  |  |
| common portion | citric acid | as appropriate | as appropriate | as appropriate | as appropriate | as appropriate | as appropriate | as appropriate |
|  | water | rest | rest | rest | rest | rest | rest | rest |
|  | pH | 6.0 | 6.0 | 6.0 | 6.0 | 6.0 | 6.0 | 6.0 |
|  | total (wt %) | 100.0 | 100.0 | 100.0 | 100.0 | 100.0 | 100.0 | 100.0 |
|  | surfactant solid content percentage (%) | 10.0 | 10.0 | 10.0 | 10.0 | 10.0 | 10.0 | 10.0 |
|  | weight ratio (A + B)/C | — | — | — | — | — | — | — |
| sense of use evaluation results | (1) fineness of foam | C | C | C | B | B | C | C |
|  | (2) foam retention | B | B | B | B | B | B | B |
|  | (3) smooth feeling after washing | C | B | A | A | A | A | A |
|  | (4) lather amount after rubbing | C | B | B | B | B | A | A |

TABLE 4-continued

|  |  | Comp. Ex. 8 | Comp. Ex. 9 | Comp. Ex. 10 | Comp. Ex. 11 | Comp. Ex. 12 | Comp. Ex. 13 | Comp. Ex. 14 |
|---|---|---|---|---|---|---|---|---|
|  | (5) low temperature stability | C | C | C | C | C | C | C |
|  | (6) clogging of mesh under low temperature conditions | C | C | C | C | C | C | C |
| Comprehensive evaluation |  | C | C | C | C | C | C | C |

| | | Comp. Ex. 8 | Comp. Ex. 9 | Comp. Ex. 10 | Comp. Ex. 11 | Comp. Ex. 12 | Comp. Ex. 13 | Comp. Ex. 14 |
|---|---|---|---|---|---|---|---|---|
| component (A) | sodium cocoyl glutamate *1 | 10.0 | 6.6 | 6.6 | 6.6 | 6.6 | 6.6 | 6.6 |
| component (B) | potassium cocoyl glycinate *2 | 5.0 | 3.3 | 3.3 | 3.3 | 3.3 | 3.3 | 3.3 |
| component (C) | lauramide propylbetaine *4 | | 5.0 | | | | | |
| | disodium cocoamphodiacetate *5 | | | 5.0 | | | | |
| | sodium cocoamphoacetate *6 | | | | 5.0 | | | |
| | sodium lauroamphoacetate *7 | | | | | 5.0 | | |
| | cocobetaine *8 | | | | | | 5.0 | |
| | lauramide propylhydroxy-sultaine *10 | | | | | | | 5.0 |
| common portion | citric acid | as appropriate | as appropriate | as appropriate | as appropriate | as appropriate | as appropriate | as appropriate |
| | water | rest | rest | rest | rest | rest | rest | rest |
| | pH | 6.0 | 6.0 | 6.0 | 6.0 | 6.0 | 6.0 | 6.0 |
| total (wt %) | | 100.0 | 100.0 | 100.0 | 100.0 | 100.0 | 100.0 | 100.0 |
| surfactant solid content percentage (%) | | 15.0 | 15.0 | 15.0 | 15.0 | 15.0 | 15.0 | 15.0 |
| weight ratio (A + B)/C | | — | 2.0 | 2.0 | 2.0 | 2.0 | 2.0 | 2.0 |
| sense of use evaluation results | (1) fineness of foam | A | A | A | A | A | A | B |
| | (2) foam retention | C | C | C | B | A | B | B |
| | (3) smooth feeling after washing | A | A | A | A | A | A | A |
| | (4) lather amount after rubbing | B | A | A | A | A | A | A |
| | (5) low temperature stability | C | B | B | C | C | C | B |
| | (6) clogging of mesh under low temperature conditions | C | B | B | C | C | C | B |
| Comprehensive evaluation | | C | B | B | C | C | C | B |

TABLE 5

| | | Comp. Ex. 15 | Comp. Ex. 16 | Comp. Ex. 17 | Comp. Ex. 18 | Comp. Ex. 19 | Comp. Ex. 20 | Comp. Ex. 21 | Comp. Ex. 22 | Comp. Ex. 23 | Comp. Ex. 24 | Comp. Ex. 25 | Comp. Ex. 26 | Comp. Ex. 27 |
|---|---|---|---|---|---|---|---|---|---|---|---|---|---|---|
| component (A) | sodium cocoyl glutamate *1 | 8.4 | 8.2 | 8.0 | 7.3 | 6.0 | 5.1 | 3.3 | 0.9 | 6.6 | 6.6 | 6.6 | 6.6 | 6.0 |
| component (B) | potassium cocoyl glycinate *2 | 4.2 | 4.1 | 4.0 | 3.6 | 3.0 | 2.4 | 1.6 | 0.4 | 3.3 | 3.3 | 3.3 | 3.3 | 3.0 |

TABLE 5-continued

|  |  | Comp. Ex. 15 | Comp. Ex. 16 | Comp. Ex. 17 | Comp. Ex. 18 | Comp. Ex. 19 | Comp. Ex. 20 | Comp. Ex. 21 | Comp. Ex. 22 | Comp. Ex. 23 | Comp. Ex. 24 | Comp. Ex. 25 | Comp. Ex. 26 | Comp. Ex. 27 |
|---|---|---|---|---|---|---|---|---|---|---|---|---|---|---|
| component (C) | cocamide propylbetaine *3 | 2.3 | 2.7 | 3.0 | 4.0 | 6.0 | 7.4 | 10.0 | 13.6 | 5.0 | 5.0 | 5.0 | 5.0 | 6.0 |
| component (E) | glycerin |  |  |  |  |  |  |  |  |  |  |  |  |  |
| component (F) | polysorbate 20 |  |  |  |  |  |  |  |  |  |  |  |  |  |
| component (G) | NaCl |  |  |  |  |  |  |  |  |  |  |  |  | 1.5 |
| common portion | citric acid | as appropriate | as appropriate | as appropriate | as appropriate | as appropriate | as appropriate | as appropriate | as appropriate | as appropriate | as appropriate | as appropriate |  | as appropriate |
|  | KOH |  |  |  |  |  |  |  |  |  |  |  | as appropriate |  |
|  | water | rest | rest | rest | rest | rest | rest | rest | rest | rest | rest | rest | rest | rest |
|  | pH | 6.0 | 6.0 | 6.0 | 6.0 | 6.0 | 6.0 | 6.0 | 6.0 | 5.0 | 5.5 | 6.5 | 13.9 | 6.0 |
|  | total (wt %) | 100.0 | 100.0 | 100.0 | 100.0 | 100.0 | 100.0 | 100.0 | 100.0 | 100.0 | 100.0 | 100.0 | 100.0 | 100.0 |
|  | surfactant solid content percentage (%) | 15.0 | 15.0 | 15.0 | 15.0 | 15.0 | 15.0 | 15.0 | 15.0 | 15.0 | 15.0 | 15.0 | 15.0 | 15.0 |
|  | weight ratio (A + B)/C | 5.5 | 4.6 | 4.0 | 2.7 | 1.5 | 1.0 | 0.5 | 0.1 | 2.0 | 2.0 | 2.0 | 2.0 | 1.5 |
| sense of use evaluation results | (1) fineness of foam | A | A | A | A | A | A | A | A | C | A | A | C | A |
|  | (2) foam retention | A | B | B | B | B | A | B | C | C | B | B | C | B |
|  | (3) smooth feeling after washing | B | A | A | A | A | A | A | A | A | A | A | B | A |
|  | (4) lather amount after rubbing | A | A | A | A | A | A | B | C | A | A | A | C | A |
|  | (5) low temperature stability | C | C | C | B | B | C | B | C | C | C | B | A | B |
|  | (6) clogging of mesh under low temperature conditions | C | C | C | B | B | C | B | C | C | C | B | C | B |
| Comprehensive evaluation |  | C | C | C | B | B | C | B | C | C | C | B | C | B |

TABLE 6

|  |  | Ex. 30 | Ex. 31 | Ex. 32 | Comp. Ex. 28 | Comp. Ex. 29 | Comp. Ex. 30 |
|---|---|---|---|---|---|---|---|
| component (A) | disodium cocoyl glutamate *11 | 6.0 | 6.0 | 6.0 | 6.0 | 6.0 | 6.0 |
| component (B) | potassium cocoyl glycinate *12 | 2.1 | 2.1 | 2.1 | 2.1 | 3.0 | 2.1 |
| component (C) | cocamide propylbetaine *3 | 6.0 | 6.0 | 6.0 | 6.0 | 6.0 | 6.0 |
| component (D) | coconut oil fatty acid K salt *12 | 0.9 | 0.9 | 0.9 | 0.9 | 0.9 | 0.9 |
| component (E) | glycerin | 3.0 |  |  |  | 3.0 |  |
|  | DPG |  |  |  |  |  | 3.0 |
|  | BG |  |  |  |  |  |  |
| component (F) | polysorbate 20 |  | 1.0 |  |  |  |  |
| common portion | citric acid |  |  |  |  | as appropriate | as appropriate |
|  | KOH | as appropriate | as appropriate | as appropriate | as appropriate |  |  |
|  | water | rest | rest | rest | rest | rest | rest |
|  | pH | 9.0 | 9.0 | 9.0 | 6.0 | 6.0 | 6.0 |
| total (wt %) |  | 100.0 | 100.0 | 100.0 | 100.0 | 100.0 | 100.0 |
| surfactant solid content percentage (%) |  | 14.1 | 14.1 | 14.1 | 15.0 | 15.0 | 15.0 |
| weight ratio (A + B)/C |  | 1.4 | 1.4 | 1.4 | 1.4 | 1.5 | 1.4 |

TABLE 6-continued

|  |  | Ex. 30 | Ex. 31 | Ex. 32 | Comp. Ex. 28 | Comp. Ex. 29 | Comp. Ex. 30 |
|---|---|---|---|---|---|---|---|
| sense of use evaluation results | (1) fineness of foam | A | B | A | A | A | A |
|  | (2) foam retention | A | A | B | B | B | B |
|  | (3) smooth feeling after washing | A | A | A | A | A | A |
|  | (4) lather amount after rubbing | A | A | A | A | A | A |
|  | (5) low temperature stability | A | A | A | B | B | B |
|  | (6) clogging of mesh under low temperature conditions | A | A | A | B | B | B |
| Comprehensive evaluation |  | A | A | A | B | B | B |

For Examples 1, 5, 9, 20, 24, 29, 30, 32 and Comparative Example 23, the viscosity of the samples was measured in the laboratory set at 25° C. A type B viscometer manufactured by Toyo Seiki Seisaku-sho Co., Ltd. was used to measure the viscosity of the samples. The sample was filled in a predetermined glass vial container and allowed to stand sufficiently at room temperature before measurement. The measurement conditions were set to rotor No: 20, rotation speed: 30 rpm, and measurement time: 30 sec, the measurement was performed, and the results are also shown in Table 7.

TABLE 7

|  |  | Ex. 1 | Ex. 5 | Ex. 9 | Ex. 20 | Ex. 24 | Ex. 29 | Ex. 30 | Ex. 32 | Comp. Ex. 23 |
|---|---|---|---|---|---|---|---|---|---|---|
| component (A) | sodium cocoyl glutamate | 6.6 | 6.6 | 8.4 | 4.8 | 6.6 | 6.6 |  |  | 6.6 |
|  | disodium cocoyl glutamate |  |  |  |  |  |  | 6.0 | 6.0 |  |
| component (B) | potassium cocoyl glycinate | 3.3 | 3.3 | 4.2 | 2.4 | 3.3 | 3.3 | 2.1 | 2.1 | 3.3 |
| component (C) | cocamide propylbetaine | 5.0 |  | 2.3 | 7.8 | 5.0 | 5.0 | 6.0 | 6.0 | 5.0 |
|  | sodium lauroamphoacetate |  | 5.0 |  |  |  |  |  |  |  |
| component (D) | coconut oil fatty acid K salt |  |  |  |  |  |  | 0.9 | 0.9 |  |
| component (E) | glycerin |  |  |  |  |  |  |  | 3 |  |
| common portion | citric acid |  |  |  | as appropriate |  |  |  |  | as appropriate |
|  | KOH | as appropriate | as appropriate | as appropriate |  | as appropriate | as appropriate | as appropriate | as appropriate |  |
|  | water | rest | rest | rest | rest | rest | rest | rest | rest | rest |
| pH |  | 9.0 | 9.0 | 9.0 | 7.0 | 8.0 | 11.0 | 9.0 | 9.0 | 5.0 |
| total (wt %) |  | 100.0 | 100.0 | 100.0 | 100.0 | 100.0 | 100.0 | 100.0 | 100.0 | 100.0 |
| viscosity [mPa·s] |  | <100 | <100 | <100 | <100 | <100 | <100 | <100 | <100 | 158.9 |

In each of the Examples, a smooth feeling was obtained after washing, the lather amount after rubbing the foam discharged from the foamer container was good, clogging during long-term use could be prevented, and low temperature stability was superior.

The numbers marked with * represent the following commercially available products.

TABLE 8

| | component name | trade name | supplier |
|---|---|---|---|
| *1 | disodium cocoyl glutamate sodium cocoyl glutamate | AMISOFT ®CS-22 | Ajinomoto Co., Inc. |
| *2 | potassium cocoyl glycinate | AMILITE ®GCK-12K | Ajinomoto Co., Inc. |
| *3 | cocamide propylbetaine | Softazoline CPB | Kawaken Fine Chemicals Co., Ltd. |
| *4 | lauramide propylbetaine | Softazoline LPB | Kawaken Fine Chemicals Co., Ltd. |
| *5 | disodium cocoamphodiacetate | MIRANOL C2M CONC NP | Rhodia |
| *6 | sodium cocoamphoacetate | Softazoline CH | Kawaken Fine Chemicals Co., Ltd. |
| *7 | sodium lauroamphoacetate | Softazoline LHL | Kawaken Fine Chemicals Co., Ltd. |
| *8 | cocobetaine | Obazorin BC | TOHO Chemical Industry Co., Ltd. |
| *9 | lauryl hydroxysultaine | AMPHITOL 20HD | Kao Corporation |
| *10 | lauramide propylhydroxysultaine | Softazoline LSB-R | Kawaken Finechemical |
| *11 | disodium cocoyl glutamate | AMISOFT ®ECS-22W | Ajinomoto Co., Inc. |
| *12 | potassium cocoyl glycinate coconut oil fatty acid potassium salt | AMILITE ®GCK-12H | Ajinomoto Co., Inc. |

TABLE 9

(Formulation Example 1)
foamy body wash

| product name | (wt %) |
|---|---|
| disodium cocoyl glutamate (30%) | 15.5 |
| potassium cocoyl glycinate (30%) | 5.5 |
| sodium lauroamphoacetate (32%) | 9.4 |
| potassium cocoate (30%) | 2.3 |
| palmitic acid | 0.1 |
| stearic acid | 0.1 |
| glycerin | 4.0 |
| PG | 3.0 |
| PPG-6 decyltetradeceth-30 | 0.1 |
| polyquaternium-10 | 0.1 |
| PCA-Na | 1.0 |
| water | rest |
| antiseptic | q.s. |
| KOH | as appropriate |
| flavor | q.s. |
| total | 100.0 |

TABLE 10

(Formulation Example 2)
foamy facial cleanser

| product name | (wt %) |
|---|---|
| sodium cocoyl glutamate (30%) | 8.8 |
| potassium cocoyl glycinate (30%) | 3.1 |
| lauryl betaine (35%) | 8.6 |
| potassium cocoate (30%) | 1.3 |
| arginine cocoate (30%) | 3.3 |
| glycerin | 12.0 |
| DPG | 9.0 |
| decylglucoside (50%) | 4.0 |
| sorbitol (70%) | 8.6 |
| polyquaternium-39 (10%) | 0.1 |
| water | rest |
| antiseptic | q.s. |
| KOH | 0.9 |
| flavor | q.s. |
| | 100.0 |

INDUSTRIAL APPLICABILITY

The liquid cleansing agent of the present invention is superior in foam quality and sense of use and is stable even at low temperatures. Therefore, it is useful as a cleansing agent to be used in a foamer container.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A liquid cleansing agent, comprising:
(A) 2 wt % to 10 wt % of at least one N-acyl glutamic acid or a salt thereof;
(B) 1 wt % to 10 wt % of at least one cocoyl glycine or a salt thereof; and
(C) 1 wt % to 20 wt % of at least one amphoteric surfactant, and
having a viscosity at 25° C. of less than 150 mPa·s and a pH of from 7 to 13,
wherein the component (C) is at least one member selected from the group consisting of cocamide propylbetaine, lauramide propylbetaine, disodium cocoamphodiacetate, sodium cocoamphoacetate, sodium lauroamphoacetate, cocobetaine, lauryl hydroxysulfobetaine, and lauramide propylhydroxysulfobetaine,
wherein a weight ratio of a total content of the components (A) and (B) to the content of the component (C), ((A)+(B))/(C), is from 0.4 to 10, and
which is contained in a foamer container.

2. The liquid cleansing agent according to claim 1, wherein the pH is 8 to 11.

3. The liquid cleansing agent according to claim 1, wherein the acyl group of the component (A) is a cocoyl group.

4. The liquid cleansing agent according to claim 1, wherein a weight ratio of a total content of the components (A) and (B) to the content of the component (C) ((A)+(B))/(C) is from 1 to 4.

5. The liquid cleansing agent according to claim 1, wherein the content of the component (A) is from 3 wt % to 8.4 wt %.

6. The liquid cleansing agent according to claim 1, wherein the content of the component (B) is from 1 wt % to 4 wt %.

7. The liquid cleansing agent according to claim 1, wherein the content of the component (C) is from 2 wt % to 12 wt %.

8. The liquid cleansing agent according to claim 1, further comprising component (D) at least one fatty acid or a salt thereof.

9. The liquid cleansing agent according to claim 1, further comprising component (E) at least one polyhydric alcohol.

10. The liquid cleansing agent according to claim 1, further comprising component (F) at least one non-ionic surfactant.

11. The liquid cleansing agent according to claim 1, further comprising component (G) sodium chloride.

12. The liquid cleansing agent according to claim 8, wherein a weight ratio of a content of the component (D) to the content of the component (B), (D)/(B), is from more than 0 to 3.

13. A method of cleansing skin or hair, comprising applying the liquid cleansing agent of claim 1 to skin or hair.

* * * * *